US006669636B2

(12) United States Patent
van Klooster

(10) Patent No.: US 6,669,636 B2
(45) Date of Patent: Dec. 30, 2003

(54) ULTRASOUND TRANSMITTER AND/OR RECEIVER SYSTEM

(75) Inventor: Jeroen Martin van Klooster, DJ Tiel (NL)

(73) Assignee: Krohne A.G., Basel (CH)

( * ) Notice: Subject to any disclaimer, the term of this patent is extended or adjusted under 35 U.S.C. 154(b) by 0 days.

(21) Appl. No.: 10/238,697

(22) Filed: Sep. 10, 2002

(65) Prior Publication Data

US 2003/0055340 A1 Mar. 20, 2003

(30) Foreign Application Priority Data

Sep. 14, 2001 (DE) ........................................ 101 45 429
Oct. 31, 2001 (DE) ........................................ 101 53 297

(51) Int. Cl.[7] ................................................ A61B 8/00
(52) U.S. Cl. ...................................................... 600/437
(58) Field of Search ................................ 600/437–471; 73/620–650; 367/7, 11, 130, 138

(56) References Cited

U.S. PATENT DOCUMENTS 5,159,838 A * 11/1992 Lynnworth .................. 73/644

FOREIGN PATENT DOCUMENTS

WO WO 96/41157 12/1996
WO WO 98/19296 5/1998

* cited by examiner

*Primary Examiner*—Ali M. Iman
(74) *Attorney, Agent, or Firm*—Cesari and McKenna, LLP

(57) ABSTRACT

An ultrasound transmitter and/or receiver/transceiver system includes an ultrasound transducer, an ultrasound waveguide and a jacket, where said ultrasound waveguide is positioned within the jacket, the ultrasound transducer is located at one end of the ultrasound waveguide and at said end of the ultrasound waveguide, the ultrasound transducer can transfer ultrasound waves to, and receive them from, the ultrasound waveguide. An impedance step is provided between the ultrasound transducer and the area of the jacket facing away from the ultrasound transducer. In this fashion, when the ultrasound transmitter and/or receiver system per the invention is installed for instance in the measuring tube of a measuring device, undesirable cross coupling and crosstalk can be sharply reduced.

4 Claims, 5 Drawing Sheets

ULTRASOUND TRANSMITTER AND/OR RECEIVER SYSTEM

RELATED APPLICATION

Not Applicable

BACKGROUND OF THE INVENTION

1. Field of the Invention

This invention relates to an ultrasound transmitting and receiving system, or transceiver, including an ultrasound transducer, an ultrasound waveguide and a jacket-type enclosure, said ultrasound waveguide being housed within the enclosure while the ultrasound transducer is positioned at one end of the ultrasound waveguide, whereby at said end of the ultrasound waveguide the ultrasound transducer can receive and transfer ultrasound waves from/to the ultrasound waveguide.

Ultrasound transceivers of this type are employed for instance in ultrasonic flowmeters and in vortex flowmeters. The ultrasound transducers typically used in these designs are piezoelectric crystals that are capable of generating as well as detecting ultrasonic waves.

In principle, it would be possible to equip an ultrasound transceiver with only one ultrasound transducer for generating as well as receiving ultrasonic waves. That, however, would require positioning the ultrasound transducer directly at the point where the ultrasonic waves are to be injected or detected. This would be difficult insofar as piezoelectric crystals, typically serving as ultrasound transducers as stated above, cannot be used above a certain temperature referred to as the Curie temperature. The reason is that above this Curie temperature, the crystal no longer possesses a ferroelectric or ferromagnetic phase, the very prerequisite for the piezoelectric properties of the crystal. Yet in cases where the moving fluid whose flow rate is to be measured with the ultrasonic flowmeter is very hot to a point where its temperature exceeds the Curie temperature of the piezoelectric crystal, any reliable operation requires a certain thermal insulation of the ultrasound transducer from the hot fluid. This is why ultrasound transceivers employ ultrasound waveguides that are designed to offer both best possible thermal insulation of the ultrasound transducer from the hot fluid and, to the extent possible, a loss-free and unimpeded transfer of the ultrasound signal. In that fashion, the ultrasound waveguide can inject ultrasonic waves generated by the ultrasound transducer into the flowing fluid and the ultrasound transducer can extract ultrasonic waves from the hot fluid while the ultrasound transducer is at a spatial distance from the hot fluid and is thermally insulated from the latter at least to a certain extent.

2. Description of the Prior Art

Conventional ultrasound transceivers employ ultrasound waveguides for instance of the type described in WO 96/41157. The ultrasound waveguide in that case is constituted of a plurality of very thin, mutually parallel rods whose individual diameter is substantially smaller than the wavelength of the ultrasound signal to be transferred. The rods are typically bundled close together and fitted into a tube that provides lateral support for the rods and thus constitutes an enclosure, or jacket, for the ultrasound waveguide, the result being a compact ultrasound waveguide. For an ultrasound waveguide, WO 96/41157 also describes a design where metal plates, bent in essentially circular fashion, are interleaved at a distance from one another. These, too, are housed in a tube that constitutes an outer jacket for the ultrasound waveguide. Finally, EP 1 098 295 discloses an ultrasound waveguide that consists of a rolled-up foil tightly fitted into a metal tube. To permit the transfer of ultrasonic waves in the frequency range from 15 kHz to 20 MHz, the thickness of each layer of the foil is less than 0.1 mm. The foil typically consists of a metallic material.

What the ultrasound transceivers incorporating ultrasound waveguides of the type described have in common is that the ultrasound transducer is positioned at one end of the ultrasound waveguide in such fashion that ultrasonic waves can be injected by the ultrasound transducer into the ultrasound waveguide and/or can be received by it from the latter. The typical approach involves the direct attachment of the ultrasound transducer to one end of the ultrasound waveguide, meaning physical contact between the two. Where the ultrasound waveguide is in the form of a rolled foil as described above, the ends of the ultrasound waveguide are usually welded up and butt-faced and the ultrasound transducer is mounted on this welded-up and level end face of the ultrasound waveguide.

However, the problem with ultrasound transmitters of the type described above is that ultrasonic waves generated by the ultrasound transducer enter not only the ultrasound waveguide but the jacket encasing it as well. A similar problem is encountered when the ultrasound transducer also serves to detect ultrasonic waves, i.e. as an ultrasound receiver, in which case ultrasonic waves travel to the ultrasound transducer not only via the ultrasound waveguide but by way of the jacket as well. As a consequence, when the system includes both an ultrasound transmitter and an ultrasound receiver, it is not only ultrasonic waves transmitted and received via the ultrasound waveguide that are measured but also ultrasonic waves that travel through the jacket of the waveguide. Now if on top of that the ultrasound transceiver system is installed with its jacket, for instance, into the wall of a pipe through which flows the fluid whose flow rate is to be measured, such measurements will include not only the ultrasonic waves that penetrate the fluid, but also those waves that have propagated through the wall of the pipe from the ultrasound transmitter to the ultrasound receiver. This phenomenon is referred to as cross coupling or crosstalk and may lead to a heterodyning or even complete suppression of the actual measuring signal of interest.

The problem associated with this manifests itself even more when one realizes that, when ultrasonic waves are switched between two mutually different media, the coefficient of transmission will be as follows, disregarding any geometric factors:

$$T=4(z_1/z_2)/(1+z_1/z_2)^2$$

where $z_1$ and $z_2$ are the characteristic impedances of the first and, respectively, second medium between which the transition takes place. In the case of a transition from steel to air, the aforementioned coefficient of transmission T is approximately 0.004%. This means that a significant part of the acoustic energy, 99.996% to be exact, is lost. A major portion of this lost energy reappears in the undesirable cross coupling. Accordingly, this cross coupling or crosstalk severely affects the signal-to-noise ratio of a flowmeter that operates with an ultrasound transceiver.

SUMMARY OF THE INVENTION

It is therefore the objective of this invention to introduce an ultrasound transmitting and receiving system by means of which any undesirable cross coupling or crosstalk can be largely avoided.

With reference to the ultrasound transceiver design described above, the invention achieves that objective by means of an impedance step between the ultrasound transducer and the side of the jacket facing away from the ultrasound transducer.

This impedance jump as provided for by the invention thus covers an area of the jacket of the ultrasound transmitter in which the undesirable entry of ultrasonic waves from the ultrasound transducer into the jacket is significantly attenuated. Correspondingly, an ultrasound receiver according to the invention includes an area in which ultrasonic waves impinging on the jacket of the ultrasound receiver and conducted to the ultrasound transducer are significantly attenuated. This is because in both cases the ultrasonic waves travelling through the jacket must pass the impedance step, either as they come from or move toward the ultrasound transducer, with the magnitude of the impedance jump determining the degree of attenuation of the intensity of the ultrasonic waves essentially along the formula shown above for the coefficient of transmission.

An impedance step as provided for by the invention in the jacket of the ultrasound transceiver can be implemented in various ways. For example, in one preferred embodiment of the invention, the jacket is positioned at a distance from the ultrasound transducer. In this fashion, an air gap is created next to the end of the jacket facing the ultrasound transducer which, as explained above with reference to the coefficient of transmission, results in a very substantial attenuation. In this connection, in a further preferred refinement of the invention, that gap is filled with a material that is different from the material of the jacket and of the ultrasound transducer. This is particularly desirable when a geometrically uniform transition from the ultrasound transducer to the jacket of the ultrasound transceiver is required, prohibiting the use of a recess.

As an alternative approach, another preferred embodiment of the invention provides for an impedance step within the jacket itself. This impedance step is attainable, for instance, by means of a recess in the jacket. As an example, the recess may be in the form of one or several drill holes. These may be blind holes or even through-holes extending through the entire thickness of the jacket. The recess may also be in the form of a preferably circumferential groove. The groove as well may extend through the entire thickness of the jacket, or only through part of the thickness of the jacket. Significantly, it is possible in this context to provide a groove whose depth varies along its circumferential extent.

If the impedance step is created in the jacket itself by means of a recess within the jacket, that recess can again be filled at least in part with a material that is different from that of the jacket and that of the ultrasound transducer.

In another preferred implementation of the invention, the ultrasound transceiver is employed in a measuring device with a vessel containing or conducting a fluid such as a gas or a liquid. A vessel containing or conducting a fluid would primarily be a tank or a pipe. An example of a vessel conducting a fluid would be a pipe equipped with an ultrasound flowmeter. In a flowmeter of that type, a preferred embodiment of the invention provides for an ultrasound transmitter and/or an ultrasound receiver, both as described above, to be mounted in the wall of the vessel above the area of the jacket that faces away from the ultrasound transducer. Thus, in the case of an ultrasound transmitter, only that part of the jacket is in contact with the wall in which the ultrasonic waves have already been significantly attenuated. The undesirable crosstalk via the wall of the vessel is substantially reduced. Conversely, in the case of an ultrasound receiver ultrasonic waves may enter by cross coupling via the wall of the vessel into that area of the jacket above which the ultrasound receiver is mounted in the wall of the vessel. But because of the impedance jump that separates this area from the region leading to the ultrasound transducer, the latter will pick up only a substantially reduced crosstalk component.

It would be entirely possible to mount the ultrasound transmitter and/or the ultrasound receiver directly in the wall of the vessel. In a preferred embodiment, however, a flange is provided for attaching the ultrasound transmitter and/or the ultrasound receiver, with additional crosstalk attenuation attainable by means of an attenuator ring installed between the flange and the jacket of the ultrasound transmitter and/or ultrasound receiver. In selecting the material for the attenuator ring an effort should again be made to obtain the largest possible impedance step. Since the jacket of the ultrasound transceiver typically consists of a metal and the wall of the vessel on its part is usually made of a metal, the material chosen for the attenuator ring would typically be a type of plastic or rubber.

BRIEF DESCRIPTION OF THE DRAWINGS

In specific terms, there are numerous ways to configure and further refine the ultrasound transmitter and/or receiver according to the invention. In this connection, reference is made to the dependent patent claims and to the following detailed description of preferred embodiments of the invention with the aid of the illustrations, in which:

DETAILED DESCRIPTION OF PREFERRED EMBODIMENTS

Figure 1A:
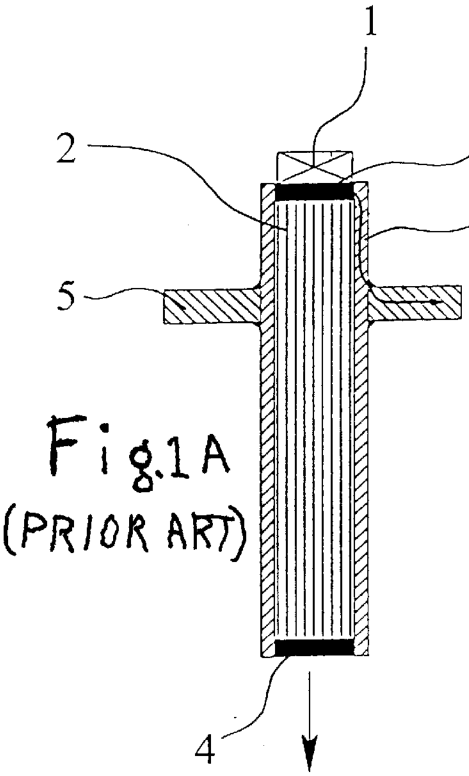
Fig.1A (PRIOR ART)
FIG. 1A shows a conventional ultrasound transceiver system.
Figure 1B:
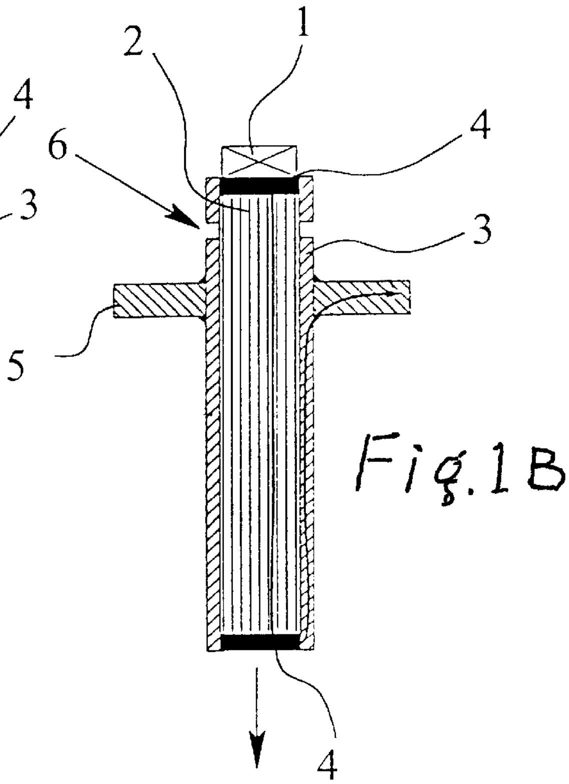
FIG. 1B shows an ultrasound transceiver system according to a first preferred embodiment of the invention as compared to a conventional ultrasound transceiver system.

Illustrated in FIG. 1B is an ultrasound transceiver system according to a first preferred embodiment of the invention to be compared with a conventional ultrasound transceiver concept depicted in FIG. 1A. The ultrasound transceiver according to the first preferred embodiment of the invention shown in FIG. 1B, includes an ultrasound transducer 1, an ultrasound waveguide 2 and a jacket 3 that encases the ultrasound waveguide 2. The ultrasound waveguide 2 consists of a thin, rolled-up metal foil about 0.1 mm thick, with its ends 4 welded up and machined flat. For mounting the ultrasound transceiver according to the first preferred embodiment of the invention, a flange 5 is welded onto the jacket 3. By way of this flange 5, the ultrasound transceiver according to the first preferred embodiment of the invention can be attached, in a way not illustrated in FIG. 1A, for instance to an adapter flange provided on a measuring tube. Like the ultrasound waveguide 2, the jacket 3 is made of metal. Above the flange 5, i.e. in an area of the jacket 3 facing the ultrasound transducer 1, the jacket 3 features a recess 6. This recess 6 is in the form of a circumferential groove, extending over the entire thickness of the jacket 3.

The conventional ultrasound transceiver depicted in FIG. 1A has no such recess. Other than that, the design of the conventional ultrasound transceiver is virtually identical. However, by virtue of the recess 6 provided in the ultrasound transceiver according to the first preferred embodiment of the invention, a totally different operational performance of the ultrasound transceiver in terms of the ultrasound waves injected by the ultrasound transducer 1 into the jacket 3 is made possible.

Specifically, as indicated by the arrows in FIG. 1A, it is possible in the conventional ultrasound transceiver for ultrasound waves injected into the jacket 3 to be transferred straight through the flange 5 and into the wall of the measuring tube, not illustrated, in which the ultrasound transceiver is installed. In contrast thereto, in the ultrasound transceiver according to the first preferred embodiment of the invention shown in FIG. 1B, any such direct path through the jacket 3 that bounds on the ultrasound transducer 1 is essentially blocked by the recess 6 in the jacket 3. It follows that ultrasound waves can reach the wall of the measuring tube, not illustrated, via the flange 5 only after having traveled through all of the ultrasound waveguide 2 where, at the end 4 of the latter, facing away from the ultrasound transducer 1, they enter the jacket 3, followed by their return flow in the jacket 3 in the direction of the ultrasound transducer 1 and finally their entry into the flange 5 as shown by the arrows in FIG. 1B. This not only reduces to a substantial extent the intensity of the ultrasound waves that enter the measuring tube through the flange 5 but it also significantly extends the run length of the crosstalk-inducing ultrasound waves; as a consequence, the interference signal emanating from the cross coupling can be expected to trail by a considerable amount of time the actual measuring signal that runs from the ultrasound transmitter straight to the ultrasound receiver. This substantially facilitates differentiating between the measuring signal and any noise.

Figure 2:
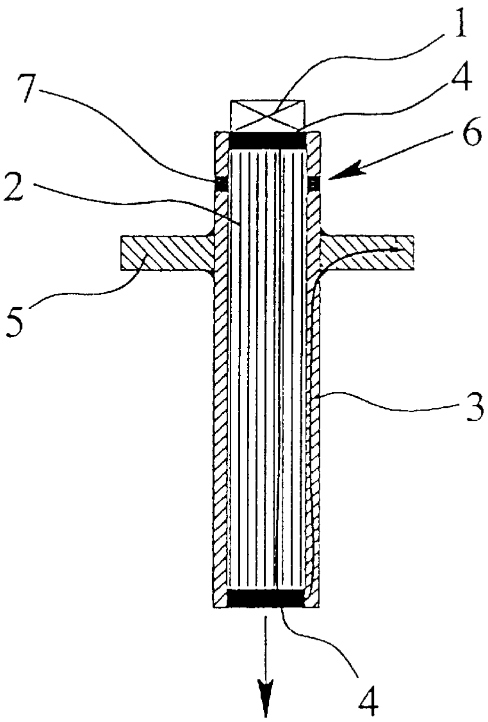
FIG. 2 shows an ultrasound transceiver system according to a second preferred embodiment of the invention.

FIG. 2 illustrates an ultrasound transceiver according to a second preferred embodiment of the invention. Its configuration is essentially identical to that of the ultrasound transceiver according to the first preferred embodiment of the invention, shown in FIG. 1B, except for the fact that the recess 6 is filled with a material 7 that differs from the material of the jacket 3 and that of the ultrasound transducer 1. In this particular case, a plastic material has been chosen for filling the recess 6.

Figure 3A:
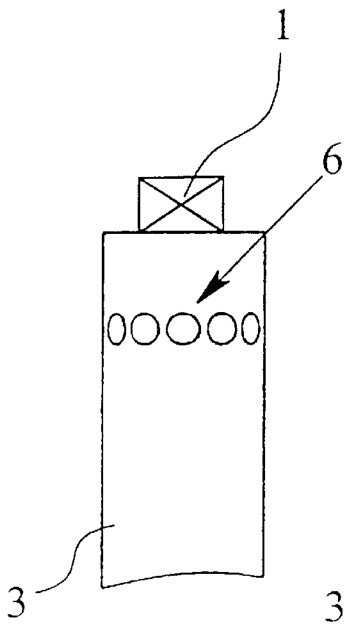
FIGS. 3A to 3C illustrate modifications of the recess in the jacket of the ultrasound transceiver according to the first or second preferred embodiment of the invention.
Figure 3B:
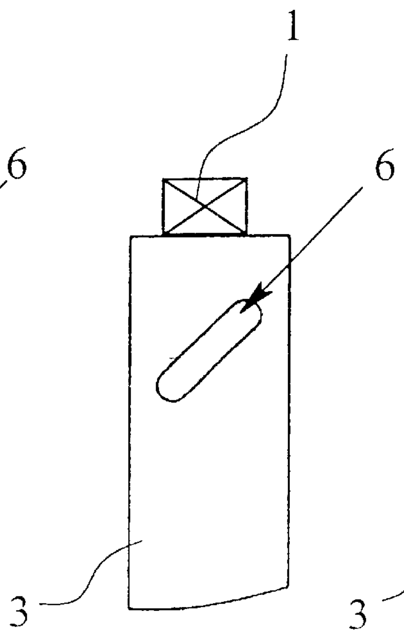
Figure 3C:
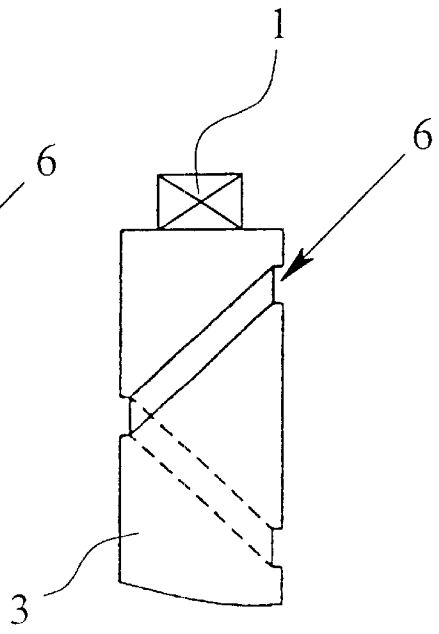

FIGS. 3A to 3C show other ways in which the recesses 6 can be provided in the jacket 3 of the ultrasound transceivers discussed. Specifically, the recess 6 may be in the form of holes (FIG. 3A), of diagonal grooves extending over part of the circumference of the jacket (FIG. 3B), or of a diagonal groove extending over the entire circumference of the jacket 3 (FIG. 3C).

Figure 4:
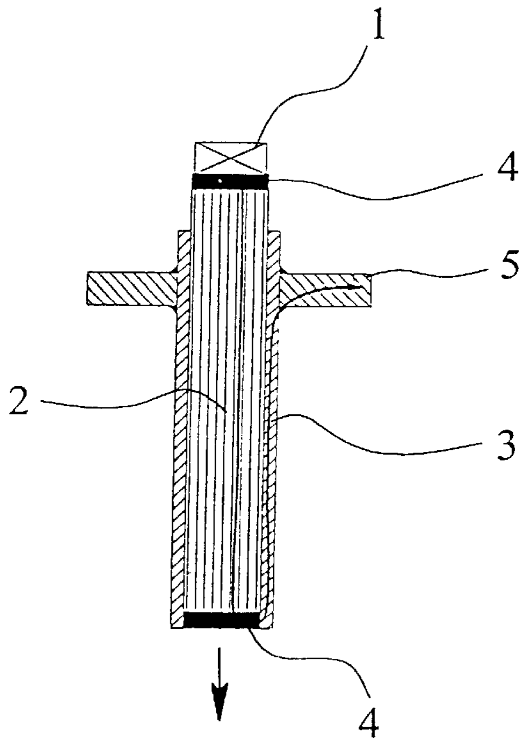
FIG. 4 shows an ultrasound transceiver system according to a third preferred embodiment of the invention.
Figure 5:
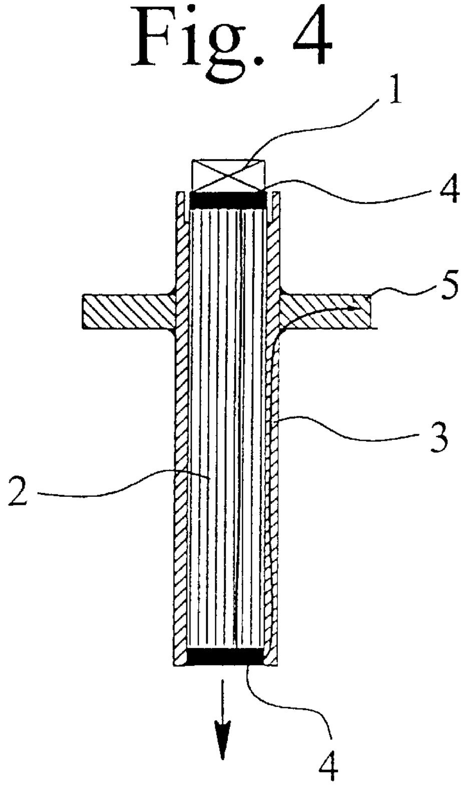
FIG. 5 shows an ultrasound transceiver system according to a fourth preferred embodiment of the invention.

FIGS. 4 and 5 depict ultrasound transceivers according to a third and, respectively, a fourth preferred embodiment of the invention. In both cases, the impedance step is not provided in the jacket 3 proper of the ultrasound transceiver but between the ultrasound transducer 1 and the jacket 3. This is because in both cases the jacket 3 does not reach all the way to the ultrasound transducer 1, meaning that it is positioned at a distance from the ultrasound transducer 1. The fourth preferred embodiment of the invention illustrated in FIG. 5 actually offers an advantage insofar as the more elongated jacket 3 provides better protection for the end 4 of the ultrasound waveguide 2 facing the ultrasound transducer 1 and for the ultrasound transducer 1 itself.

Figure 6:
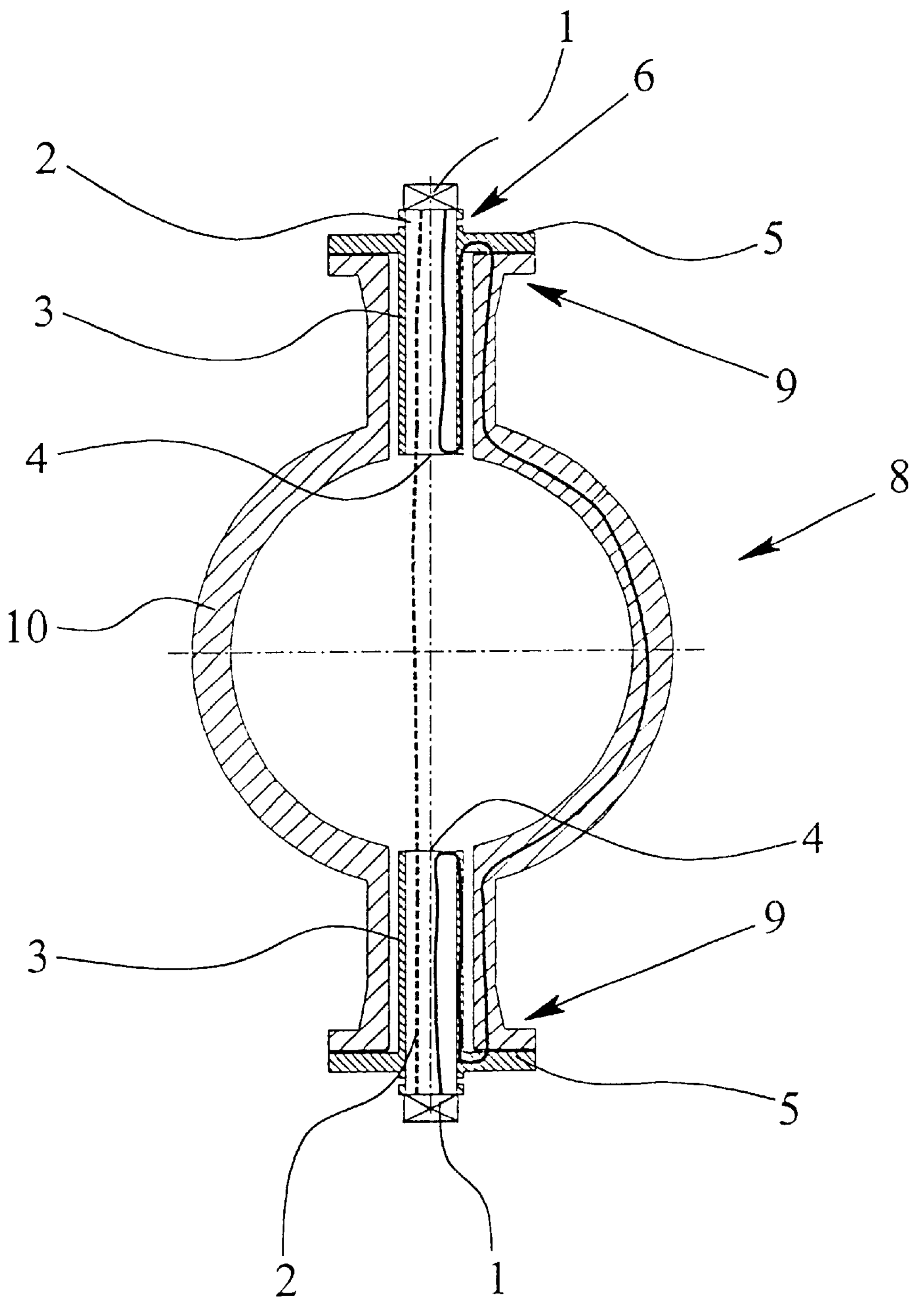
FIG. 6 depicts the installation of ultrasound transceivers according to the first preferred embodiment of the invention in the measuring tube of an ultrasonic flowmeter.

FIG. 6 shows the manner in which ultrasound transceivers according to the above-described first preferred embodiment of the invention are installed in the measuring tube 8 of an ultrasonic flowmeter, i.e. in each case by way of an adapter flange 9. As can be seen in FIG. 6, the path traveled by the crosstalk-inducing ultrasound waves from one of the ultrasound transducers 1 via the flange 5 of the ultrasound transmitter, then through one of the adapter flanges 9, the wall 10 of the measuring tube 8, the other adapter flange 9, the flange 5 of the ultrasound receiver and up to the other ultrasound transducer 1, is significantly longer than the direct path via the ends 4 of the ultrasound waveguides 2 of the ultrasound transceiver, facing away from the corresponding ultrasound transducer 1. As a consequence, the crosstalk-inducing ultrasound waves arrive later by a considerable margin than the actual measuring signal, permitting relatively easy differentiation between the measuring signal and crosstalk noise, assuming pulsed system operation.

Figure 7:
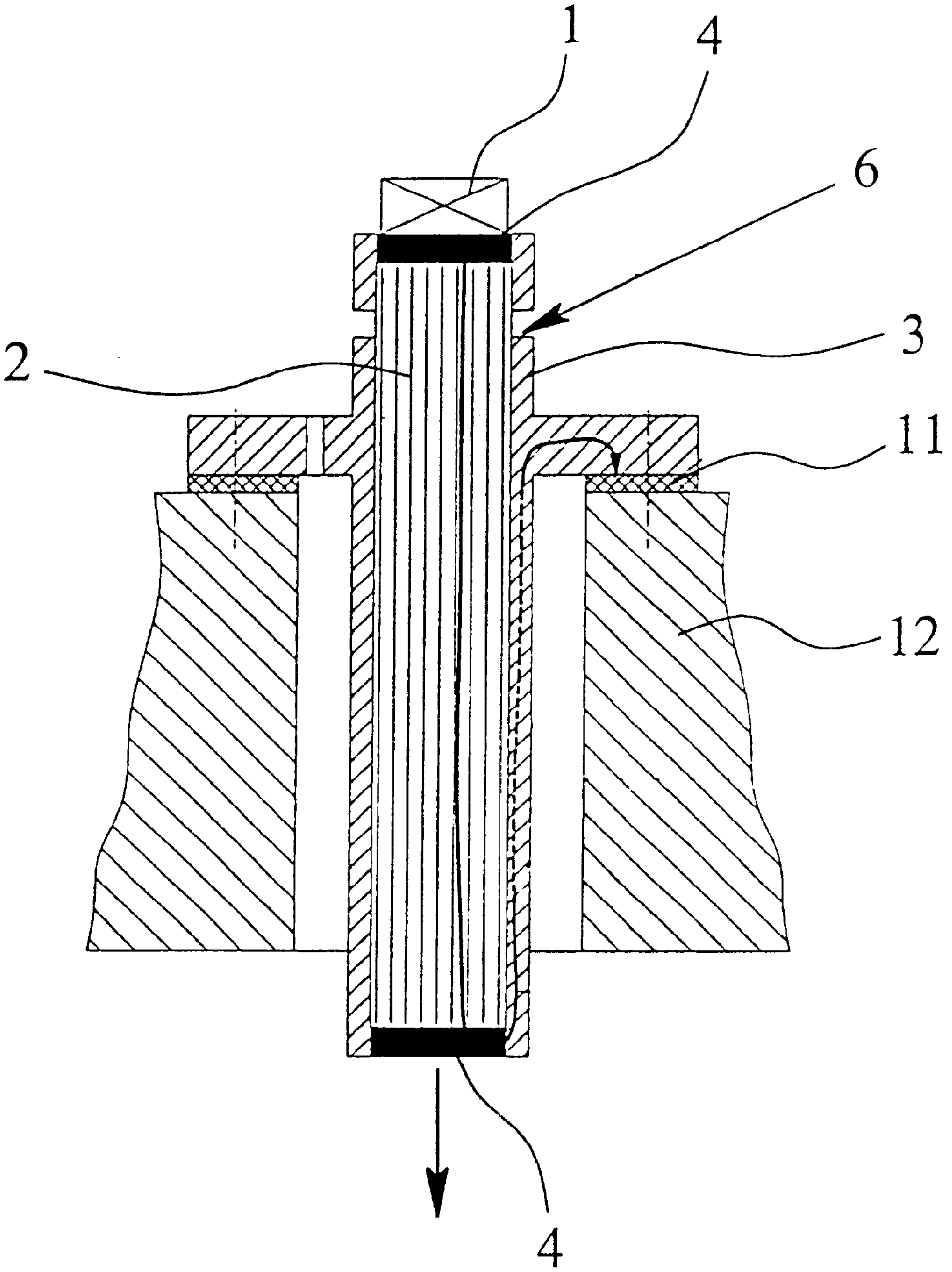
FIG. 7 illustrates the positioning of the ultrasound transceiver system according to the first preferred embodiment in the wall of a vessel on top of an attenuator ring.

FIG. 7 shows the manner in which an ultrasound transceiver system according to the first preferred embodiment of the invention is installed in the wall 12 of a vessel with the interpositioning of an attenuator ring 11. In this particular case, the attenuator ring 11 is made of rubber, providing added attenuation of the crosstalk-inducing ultrasound waves.

What is claimed is:

1. An ultrasound transceiver system comprising a vessel having a wall and containing or conducting a fluid;

an ultrasound waveguide having an end;

a jacket surrounding said ultrasound waveguide, said jacket having a defined area facing away from said end of the ultrasound waveguide;

an ultrasound transducer located at said one end of the ultrasound waveguide so that the ultrasound transducer can transfer ultrasound waves to, and receive them from, the ultrasound waveguide;

an impedance step between the ultrasound transducer and said defined area of the jacket, said impedance step being constituted by a circumferential groove that extends through the entire thickness of the jacket, and mounting means for at a location on the jacket between the groove and said defined area of the jacket for mounting the jacket to said vessel wall.

2. The system as in claim 1 wherein the groove is at least in part filled with a material that is different from the material of the jacket and that of the ultrasound transducer.

3. The system as in claim 1 or 2, wherein said mounting means comprise a flange extending from the jacket and an attenuator ring in contact with said flange.

4. The system as in claim 3, wherein the attenuator ring is made of plastic or rubber.

* * * * *